United States Patent

Chen et al.

[11] Patent Number: 6,162,474
[45] Date of Patent: Dec. 19, 2000

[54] VITAMIN POWDERS FOR BEVERAGE APPLICATIONS AND METHOD OF MAKING

[75] Inventors: Chyi-Cheng Chen, Wayne; William Joseph Mergens, West Caldwell; Mark Cordes Milbank, West Milford, all of N.J.

[73] Assignee: Roche Vitamins Inc., Parsippany, N.J.

[21] Appl. No.: 09/339,701

[22] Filed: Jun. 24, 1999

Related U.S. Application Data

[60] Provisional application No. 60/090,508, Jun. 24, 1998.

[51] Int. Cl.[7] ............................... A23D 9/05; A23L 1/303
[52] U.S. Cl. ............................... 426/72; 426/73; 426/98; 426/103; 426/471; 426/519; 426/590; 426/599; 426/650; 424/439; 424/464; 424/466
[58] Field of Search ........................ 426/98, 103, 471, 426/590, 599, 650, 72, 73, 519; 424/439, 464, 466

[56] References Cited

U.S. PATENT DOCUMENTS 3,971,852  7/1976  Brenner et al. ..................... 426/103
4,844,924  7/1989  Stanley .
5,616,358  4/1997  Taylor et al. ..................... 426/590

FOREIGN PATENT DOCUMENTS 239 086      9/1987   European Pat. Off. .
811 633 A2  12/1997   European Pat. Off. .
59-227243   12/1984   Japan .
1026493      4/1966   United Kingdom .
97/44009    11/1997   WIPO .

OTHER PUBLICATIONS

Oosawa Hide, "Preparation of delicious instant health drink," Patent Abstracts of Japan, Dec. 20, 1984.
Derwent Abstract of EP 239 086, Sep. 30, 1987 (B3).
Derwent Abstract of WO 97/44009, Nov. 27, 1997 (B4).

*Primary Examiner*—Helen Pratt
*Attorney, Agent, or Firm*—Mark E. Waddell; Stephen M. Haracz; Bryan Cave LLP

[57] ABSTRACT

The present invention provides a powder composition which comprises droplets of a fat soluble vitamin which droplets average about 70 to about 200 nanometers in diameter, and which are dispersed in a modified polysaccharide matrix, beverages and tablets containing the composition, and methods of making the composition.

32 Claims, 2 Drawing Sheets

VITAMIN POWDERS FOR BEVERAGE APPLICATIONS AND METHOD OF MAKING

This application claims priority under 35 U.S.C. § 119(e) of provisional application Ser. No. 60/090,508, filed Jun. 24, 1998.

BACKGROUND OF THE INVENTION

The present invention relates to powder compositions useful to produce nutritious vitamin and mineral supplemented beverages which contain vitamin E and other fat soluble vitamins. Vitamin supplements for human and veterinary use are commonplace. Some diets, or heavy physical exercise, may require the intake of considerable quantities of vitamins apart from those generally obtained through what otherwise would be considered a balanced diet.

Vitamin supplementation is also important, primarily for those who have inadequate diets, including growing children. In Central and South American countries where the dietary intake of vitamins are low in the general population, such vitamin supplement would have great value.

Sports beverages such as GATORADE®, and vitamin supplemented waters, are beverages where the addition of vitamins is of interest. Also of interest are beverages used to restore electrolytes lost through diarrhea, for example, Pedialyte®. Also of interest are carbonated beverages such as flavored seltzer waters, soft drinks or mineral drinks, as well as non-carbonated fruit and vegetable juices, punches and concentrated forms of these beverages. In supplementing such beverages, it is often desirable to preserve the optical clarity of the beverage. Fat soluble vitamins for supplementation are available in many forms, but when added to beverages, will tend to increase the visible turbidity. Ringing—the formation of a separate fat-soluble vitamin layer on the top of the liquid, is also a problem which vitamin formulations have not solved. One means of adding fat-soluble vitamins to beverages without increasing visible turbidity or ringing is to encapsulate the vitamins in liposomes. However, this is a costly process, and the concentration of active substance in the liposome tends to be low.

One object of the present invention is to provide a powder composition of fat soluble vitamins which can be added to beverages in a restorative or nutritionally supplemental amount, preferably without affecting the optical clarity of the beverage. Another object of the present invention is that the powder composition does not alter the sensory properties of the beverage to which it is added, in particular does not cause ringing, and to enhance bioavailability.

SUMMARY OF THE INVENTION

The present invention relates to a powder composition which comprises a fat soluble vitamin and a modified polysaccharide. The composition is a powder composition which comprises droplets of a fat-soluble vitamin, which droplets average about 70 to about 200 nanometers (nm) in diameter, and which are dispersed in a modified polysaccharide matrix. When this powder is added to a liquid it provides a resulting liquid containing the fat-soluble vitamin and the modified polysaccharide in droplets of about 70 to about 200 nm, preferably about 80 to about 120 nm, and most preferably about 100 nm in diameter. The composition may include a single vitamin, or more than one vitamin. The vitamin may be in pure form, or may be in a diluent such as an edible oil. Preferably, the fat-soluble vitamin is selected from the group consisting of vitamin E or its esters, vitamin A or its esters, vitamin K, and vitamin D3 and mixtures thereof. More preferably, the fat soluble vitamin is vitamin E and its esters. A process for making such a composition is also contemplated.

Powder compositions of this invention contain vitamin droplets of a very small size. As a result, the compositions can be added to a liquid without causing ringing. In addition, bioavailability may be improved. Also, preferred compositions of this invention can be added to a clear liquid without significantly increasing its turbidity.

A modified polysaccharide as used in this invention is specifically defined below. Briefly, the modified polysaccharide is a good emulsifier, e.g. having both hydrophilic (affinity to water) and lipophilic (affinity to dispersed phase) moieties. Accordingly the modified polysaccharide preferably has a long hydrocarbon moiety (a fatty acid "tail"). At least one polysaccharide is preferably used to make a composition of this invention, but it is possible to use a mixture of two or more different polysaccharides in one composition.

The invention includes emulsion compositions comprising a fat-soluble vitamin, a modified polysaccharide, and water.

The present invention is also directed to beverages, by which is meant liquids intended for human or animal consumption, containing the powder composition of this invention where the fat soluble vitamins are present in a nutritionally supplemental or restorative amount. In the case of clear beverages, the preferred beverage should have an optical clarity which does not differ significantly from its optical clarity before addition of the powder, for example which does not appear significantly more turbid on visual inspection. Typical beverage or beverage concentrate compositions comprise 0 to 100% by weight of juice and/or of flavor, a nutritionally supplemental amount of fat soluble vitamin, and a modified polysaccharide, and water if necessary to bring the weight of the beverage to 100%, and an optional sweetener. By juice is meant a product derived from pure fruit or vegetable material. The beverage may be 100% water.

These beverages can be carbonated beverages e.g., flavored seltzer waters, soft drinks or mineral drinks, as well as non-carbonated juices, punches and concentrated forms of these beverages. By way of example, the juices used herein include grape, pear, passion fruit, pineapple, banana or banana puree, apricot, orange, lemon, grapefruit, apple, cranberry, tomato, mango, papaya, lime, tangerine, cherry, raspberry, melon, carrot, cabbage, celery, cucumber, spinach, tomato, and mixtures thereof. Additionally, artificial flavors, e.g. cola, or natural flavors derived from these juices can be used in the beverages. Chocolate flavors and other non-fruit flavors can also be used to make beverages. Beverages, especially juice and cola beverages, which are carbonated in the manner of soft drinks, as well as "still" beverages and nectars and full-strength beverages or beverage concentrates which contain at least about 45% by weight of juice are also contemplated.

Effervescent tablets comprising the powder composition of this invention, e.g. a fat-soluble vitamin and a modified polysaccharide are also part of this invention, as is a method for producing the powder composition. The tablets of this invention may be dissolved in a liquid without causing ringing.

A BRIEF DESCRIPTION OF THE FIGURES

FIG. 1: Flow diagram of typical procedure for preparation of a powder composition of this invention. 1—25 liter Fryma process unit with integrated dissolve disc and colloid mill;. 2—gear pump. max. 1,000 liters/hr. man. 100 bar. 3—microfluidizer, M-210C-E/H, 100 liter/hr. max, 2,000 bar 4—heat exchanger with cold water (ca. 10° C.) 5—milk can 6—pump integrated to Minor spray dryer 7—spray dryer Minor Model Hi-Tec.

DETAILED DESCRIPTION OF THE INVENTION

The present invention relates to a powder composition which comprises a fat soluble vitamin and a modified polysaccharide, which powder composition comprises droplets of a fat-soluble vitamin, which droplets average about 70 to about 200 nanometers (nm) in diameter, and which are dispersed in a modified polysaccharide matrix. A preferred powder of this invention comprises droplets which average about 80 to about 120 nm diameter. Most preferred is a droplet size of 100 nm.

This powder, when added to a liquid, provides a liquid containing the vitamin and the modified polysaccharide with average vitamin droplet size of about 70 to 200, preferably 80 to about 120 nm in diameter. When the liquid is optically clear, then the liquid remains for all practical purposes optically clear after addition of the preferred powder composition. Preferably, the fat soluble vitamin is selected from the group consisting of vitamin E or its esters, vitamin A or its esters, vitamin K, and vitamin D3 and mixtures thereof. More preferably, the fat soluble vitamin is vitamin E and its esters.

The powder of this invention is made up of particles of fat-soluble vitamin dispersed in a modified polysaccharide matrix. These particles may be of various sizes, but all of them are at least sufficiently large to have a structure throughout which individual droplets of the fat soluble vitamin are distributed, and may be as large as several hundred microns. The vitamin droplets have an average size of about 70 to about 200 nm in diameter or even less (for example 50 nm). The droplets may contain fat soluble vitamin in a pure form, or fat soluble vitamin in a suitable medium or diluent such as edible oil. The droplets may also contain a mixture of two or more different fat-soluble vitamins. When the powder is added to a liquid, the predominant structure of the resulting droplets is a vitamin core sheathed by a modified polysaccharide interface between vitamin and the aqueous medium.

Droplet size is conveniently determined by light scattering technique using an instrument such as Malvern Zeta-Sizer 3, which provides an average droplet size (the "Z" average). This method is known in the art and described in various references (for example Particle size Distribution, ACS Symposium Series 332, Ed. T. Provder, American Chemical Society, Washington, D.C.; 1987). Thus, a powder composition of this invention contains droplets consisting of the fat soluble vitamin with droplet size average about 70 to about 200 nm in diameter by the technique of light scattering.

Optical clarity may be estimated by a visual comparison, such that if there is no significant visible added turbidity, the liquid has retained its optical clarity. Optical clarity (turbidity) can be accurately measured by turbidimeter. To determine the turbidity, a sample is dispersed, with stirring, in water or beverages. After complete dispersion, which usually takes a few minutes or more (up to complete dispersion as determined below), the turbidity of the resulting liquid is measured using a turbidimeter (available from Orbeco Analytical Systems, Inc., Farmingdale, N.Y.). Complete dispersion is indicated when a constant turbidity reading is obtained. Turbidity is measured by directing a beam of light into a cell containing the test sample, measuring the amount of light that is reflected at a 90 degree angle by any droplets present in the sample and comparing it to the light scattered by a standard reference suspension. The intensity of the light reflected at 90 degrees is measured by a suitable photodetector, amplified and displayed on a digital readout. The amount of light is directly proportional to the degree of turbidity. NTU (Nephelometric Turbidity Unit) is customarily used to describe the results from the turbidity measurement using a turbidimeter. Higher NTU means higher turbidity.

Any standard turbidimeter will provide equivalent NTU measurements. For purposes of this invention, an NTU of ten or less is optically clear. For example, the NTU of most of commercial apple juice investigated is about 5. An optically clear liquid to which a preferred powder composition of this invention has been added will preferably have a resulting NTU of no more than forty NTUs, and preferably ten to twenty NTUs. The compositions of this invention may also be added to liquids which are not optically clear. In this regard, increase in turbidity is not of concern. Ringing will not occur. Also, bioavailability of the vitamin may be increased. The invention contemplates powder compositions which when added to a liquid provide vitamin droplets averaging about 70 to about 200 nm in diameter, preferably about 80 to about 120 nm, and most preferably about 100 nm.

The modified polysaccharide as used herein has been chemically modified by known methods to be a good emulsifier in an oil in water context to emulsify the oil into a fine dispersion in the aqueous medium. Accordingly, the modified polysaccharide has been modified to have a chemical structure which provides it with a hydrophilic (affinity to water) portion and a lipophilic (affinity to dispersed phase) portion. This enables it to dissolve in the dispersed oil phase and in the continuous water phase. Preferably the modified polysaccharide has a long hydrocarbon chain as part of its structure (preferably $C_5$–$C_{18}$), and is capable of forming a stable emulsion of a desired droplet size (for example 70–200 nm) under conditions of high pressure homogenization. By high pressure is meant a pressure of about 10,000 psi to about 60,000 psi, and even higher. Modified polysaccharides are well known materials which are available commercially, or may be isolated by a skilled person using conventional methods.

Whether a polysaccharide is a modified polysaccharide as defined in this invention may be determined by assaying whether it can maintain an emulsion as defined above by using the polysaccharide to produce a powder composition of this invention as provided below. Briefly, one starts with a crude emulsion made by dissolving the modified polysaccharide in a suitable aqueous solvent such as water and during homogenization adding fat soluble vitamins in such proportions as to produce a crude emulsion with a solids content (percent by weight of vitamin(s) and modified polysaccharide(s)) of preferably no more than 60% (a solids content of 70% is possible however may be difficult to process due to the thickness of the emulsion). The amount of lipid, or lipid content, is the lipid component of the solids content. The lipid component may be pure vitamin or vitamin in an appropriate diluent. The lipid content preferably makes up 75% by weight or less of the solids content. If the resulting emulsion has an average emulsion droplet size of about 70 to about 200 nm after one up to about one hundred cycles of emulsification (passes) at a pressure of about 10,000 to 60,000 psi, then the polysaccharide is a modified polysaccharide suitable for use in this invention. The modified polysaccharide should also produce an emulsion which remains stable at least until the performance of the next preparation step—spray drying.

A preferred modified polysaccharide is modified starch. Starches are hydrophilic and therefore do not have emulsifying capacities However, modified starches are made from starches substituted by known chemical methods with hydrophobic moieties. For example starch may be treated with cyclic dicarboxylic acid anhydrides such as succinic anhydrides, substituted with a hydrocarbon chain. (see "Modified Starches: Properties and Uses, ed. O. B. Wurzburg, CRC Press, Inc., Boca Raton, Fla. (1991)). A particularly preferred modified starch of this invention has a structure as depicted in below Formula 1 wherein St is a starch, R is an alkylene radical and R' is a hydrophobic group. Preferably the alkylene radical is lower alkylene, such as dimethylene or trimethylene. R' may be a alkyl or alkenyl group, preferably $C_5$ to $C_{18}$. A preferred compound of Formula 1 is starch sodium octenyl succinate. It is available commercially from, among other sources, National Starch and Chemical Company, Bridgewater, N.J. as Capsul®. Making this compound, and the compounds of Formula 1 in general, is known in the art (see "Modified Starches: Properties and Uses, ed. O. B. Wurzburg, CRC Press, Inc., Boca Raton, Fla. (1991))

Preferably the modified polysaccharide should be at least acceptable for animal consumption. For human consumption, preferred modified polysaccharides should be GRAS (generally recognized as safe) or an approved material for food consumption as determined by the various regulatory agencies world wide.

As fat soluble vitamins, vitamin E or its esters (for example, vitamin E acetate), vitamin A or its esters (for example, vitamin A acetate and vitamin A palmitate), vitamin K (phytomenadione) and vitamin D3 (cholecalciferol) are contemplated in the present invention. Vitamin E or its esters is the preferred fat soluble vitamin, with vitamin E acetate being most preferred. Such vitamins are readily available from commercial sources. Also, they may be prepared by conventional methods by a skilled person. Vitamins may be used in pure form, or in a suitable diluent such as a fat or oil (e.g. soybean oil). Thus the droplets in the powder of this invention may contain one or more vitamins in a pure state or in an appropriate diluent.

The composition of this invention can comprise from about 0.5 to 75% by weight of fat soluble vitamin (the "potency" of the composition) and from about 99.5 to 25% by weight of modified polysaccharide, on a dry weight basis. A preferable percent of fat soluble vitamin is from about 15% to about 40%, most preferably about 25% by weight. The composition may contain only vitamin and modified polysaccharide in percentages that add up to 100%. The composition may also contain a small amount of residual water. The amount of residual water depends on the drying technology used, which will be evident to a skilled practitioner. A typical amount of residual water is up to about 4.0% by weight. Alternately, other ingredients standard to a vitamin powder composition may be added, for example vitamin protectors such as sucrose or maltodextrin alone or in combination, and the amounts of vitamin and polysaccharide adjusted accordingly. Therefore also part of this invention is a composition where the ratio of fat soluble vitamin to modified polysaccharide is from about 1:199 to about 3:1. A preferred composition comprises from about 15 to about 40 percent by weight of fat soluble vitamin and from about 60 to 85% by weight of modified polysaccharide. A preferred ratio of fat soluble vitamin to modified polysaccharide is about 3:17 to 2:3. A preferred modified polysaccharide is a modified starch, in particular a modified starch of formula 1. In a particularly preferred composition, the fat soluble vitamin is vitamin E or vitamin E acetate and the modified polysaccharide is starch sodium octenyl succinate.

Also part of this invention is an emulsion composition containing a fat soluble vitamin and a modified polysaccharide as described above, and water, wherein the average droplet size of the emulsion is no more than about 200 nm in diameter e.g. about 50 to about 200 nm in diameter. A preferred emulsion comprises about 5% to 20% by weight of the fat-soluble vitamin, especially 7.5% to 20%, about 30% to 40% by weight of the modified polysaccharide, and about 50% to 55% of water. The emulsion may optionally contain a preservative. This emulsion is useful for preparing the powder composition of this invention. A preferred modified polysaccharide is a modified starch, in particular a starch of Formula 1. Especially preferred is starch sodium octenyl succinate. A preferred vitamin is vitamin E and its acetate. When other components such as preservatives are included, the percent vitamin, polysaccharide, and water may be adjusted accordingly.

Tablets, in particular effervescent tablets, are part of this invention. Such tablets comprise a fat soluble vitamin and a modified polysaccharide as described above, and are preferably obtained from the powder composition of this invention by formulating the composition into tablets by conventional tabletting means. When added to a liquid such as water, mineral water, or a beverage, the tablet dissolves and provides a liquid whose fat-soluble vitamin contents do not cause ringing, by which is meant separation of a top fat-soluble vitamin layer on the liquid. The tablets of this invention may be produced from any powder composition described herein, for example compositions where the preferred modified polysaccharide is a modified starch, in particular a starch of Formula 1 such as starch sodium octenyl succinate. A preferred vitamin is vitamin E and its acetate.

The present invention is also directed to beverages comprising a mixture of at least about 0% to 100% by weight of flavor and about 0% to about 100% by weight of juice, a modified polysaccharide, and a nutritionally supplemental amount of fat soluble vitamin in the form of droplets which average about 70 to about 200 nm in diameter (preferably about 80 to about 120 nm) and water if necessary to bring the beverage weight to 100%. Thus, the beverages of this invention may be 100% juice, 100% flavor, 100% water, or any combination of these components including water alone (0% flavor and 0% juice). In particular a beverage may be about 3% fruit juice and 97% water, or 0.05% flavor, 1.95% fruit juice, and 98% water. Sweeteners, preservatives, and stabilizers, and other known beverage components may be included in the beverage. When these components are included, the percent juice, flavor, and water are adjusted accordingly. This invention is also directed to a beverage comprising a mixture of at least about 0% to 100% by weight of flavor and 0% to about 100% by weight of juice, a nutritionally supplemental amount of fat soluble vitamin and modified polysaccharide and water if necessary to bring the beverage weight to 100%, which beverage has an optical clarity of no more than 20 NTUs. The beverages of this invention are preferably obtained by adding to a beverage a powder composition of this invention.

Adding a powder composition of this invention to a liquid requires no special procedure or extensive mixing. The powder may simply be added to the liquid and mixed by shaking or stirring until the powder particles are no longer visible to the naked eye. Any one or more of the powder compositions of this invention may be added to a beverage as described herein, to obtain a beverage of this invention, e.g a fortified beverage. For example, the fat soluble vitamin may be one or more of vitamin E or its esters, vitamin A or its esters, vitamin K, and vitamin D3, especially vitamin E and vitamin E acetate. The modified polysaccharide may be a modified starch such as a starch of Formula 1. A preferred starch is starch sodium octenyl succinate.

Fat soluble vitamins may be added in a restorative amount, i.e. enough vitamin to replace vitamin naturally present in a beverage such as juice or milk, which vitamin has been lost or inactivated during processing. Fat soluble vitamins may also be added in a nutritionally supplemental amount, i.e. an amount of vitamin considered advisable for a child or adult to consume based on RDAs and other such standards, preferably from about one to three times the RDA. A nutritionally supplemental amount of fat soluble vitamin may be readily determined by a skilled person to obtain the desired amount of fortification in a liquid, e.g. a beverage and based on RDAs and other such standards. A preferred amount for vitamin E is from about 5 to 30 mg of vitamin E per 8 ounces of liquid (one serving of a beverage). An especially preferred amount is 8 mg to 20 mg. Most preferred is about 15 mg per 8 ounces. Thus the powder compositions of this invention may be added to a beverage to provide a vitamin E concentration of from about 5 to 30 mg, or 8 to 20 mg per 8 ounces of liquid. Eight ounces of liquid can alternately be expressed as 240 grams. In the case of fat-soluble vitamins which have greater potency than vitamin E, it is preferred to formulate the powder composition such that 5 to 30 mg of such a vitamin in diluent (e.g. edible oil) may be added. This means that the vitamin is diluted in diluent so that 5–30 mg of vitamin in diluent provides a suitable nutritionally supplemental amount, for example a multiple of the RDA, preferably 1 to 3 times the RDA. For example the RDA for vitamin $D_3$ is 400 IU. Thus a vitamin $D_3$ composition of this invention would preferably contain 15% to 40% by weight of 400 IU of vitamin $D_3$ in diluent. The same would apply to other fat soluble vitamins. A skilled practitioner will be familiar with appropriate formulations. Alternatively, the vitamin itself in undiluted form may be used to make the powder composition, as long as the vitamin in a concentration of about 1–3 RDAs can be provided so as to constitute 0.5% to 95% by weight of the composition. Whether or not dilution is necessary will depend on the potency of the vitamin.

The amount of powder composition to be added depends on the potency of the powder, i.e. the amount of vitamin in the powder, which in this invention can range from about 0.5% to about 75% by weight. Preferred powders have potency of about 25% to about 40%. Powders with smaller droplet sizes will in general generate less turbidity in liquid. Based on the droplet size and the desired level of fortification and turbidity, the skilled person should be able to determine the amount of powder to add depending on its potency to attain desired optical clarity. If a beverage to be supplemented is already turbid, then increase in NTUs is less likely to be a concern, and a higher range of added turbidity can be accomodated. A preferred beverage of this invention contains about 8 to about 20 mg of fat soluble vitamins in the form of droplets which are about 70 to about 120 nm in diameter, especially 100 nm.

The beverages of this invention can be carbonated beverages e.g., flavored seltzer waters, soft drinks or mineral drinks, as well as non-carbonated juices, punches and concentrated forms of these beverages. Beverages, especially juice and cola beverages, which are carbonated in the manner of soft drinks, as well as "still" beverages and nectars and full-strength beverages or beverage concentrates which contain at least about 45% by weight of juice are also contemplated.

By way of example, the fruit juices and fruit flavors used here in include grape, pear, passion fruit, pineapple, banana or banana puree, apricot, orange, lemon, grapefruit, apple, cranberry, tomtato, mango, papaya, lime, tangerine, cherry, raspberry, carrot and mixtures thereof. Additionally, artificial flavors, e.g. cola, or natural flavors derived from these juices can be used in the beverages. Chocolate flavors and other non-fruit flavors can also be used to make beverages containing the vitamin and mineral supplement. Additionally, milk, obtained from cows or synthetic, is a contemplated beverage to which the powder compositions of this invention can be added. The milk may itself include other beverage components, in particular flavors such as chocolate, coffee, or strawberry. As used herein, the term "juice product" refers to both fruit and vegetable juice beverages and fruit and vegetable juice concentrates which comprise at least about 45% fruit juice. Vegetable when used herein includes both nonfruit edible plant parts such as tubers, leaves, rinds, and also if not otherwise indicated, any grains, nuts, beans, and sprouts which are provided as juices or beverage flavorings.

Sport beverages are also contemplated as beverages which can be supplemented by the powder compositions of the present invention. Typical sport beverages contain water, sucrose syrup, glucose-fructose syrup, and natural or artificial flavors. These beverages can also contain citric acid, sodium citrate, monopotassium phosphate, as well as other materials which are useful in replenishing electrolytes lost during perspiration.

As used herein, the term "juice beverage" refers to a fruit or vegetable juice product which is in a single-strength, ready-to-serve, drinkable form. Juice beverages of the present invention can be of the "full-strength" type which typically comprise at least about 95% juice. Full strength juice beverages also include those products of 100% juice such as, for example, orange, lemon, apple, raspberry, cherry, apricot, pear, grapefruit, grape, lime, tangerine, carrot, pineapple, melon, mango, papaya, passion fruit, banana and banana puree, cranberry, tomato, carrot, cabbage, celery, cucumber, spinach, and various mixtures thereof. Juice beverages also include extended juice products which are referred to as "nectars". These extended juice products typically comprise from about 50% to about 90% juice, preferably, from about 50% to about 70% juice. Nectars usually have added sugars or artificial sweeteners or carbohydrate substitutes. As used herein, the term "citrus juice" refers to fruit juices selected from orange juice, lemon juice, lime juice, grapefruit juice, tangerine juice and mixtures thereof.

As used herein, the term "juice materials" refers to concentrated fruit or vegetable juice, plus other juice materials such as juice aroma and flavor volatiles, peel oils, and pulp or pomace. As used herein, the term "juice concentrate" refers to a fruit or vegetable juice product which, when diluted with the appropriate amount of water, forms drinkable juice beverages. Juice concentrates within the scope of the present invention are typically formulated to provide drinkable beverages when diluted with 3 to 5 parts by weight water.

As used herein the term "beverage concentrate" or "bottling syrup" refers to a mixture of flavors, water and from about 10% to about 60% sugar or carbohydrate substitute, i.e. sucrose, dextrose, corn syrup solids, fructose, dextrins, polydextrose and mixtures thereof.

The flavor component of the beverages and beverage concentrates contains flavors selected from fruit flavors, vegetable flavors, botanical flavors and mixtures thereof. As used herein, the term "fruit flavor" refers to those flavors derived from the edible reproductive part of a seed plant, especially one having a sweet pulp associated with the seed, and "vegetable flavor" refers to flavors derived from other edible parts of seed and other plants. Also included within the term "fruit flavor" and "vegetable flavor" are synthetically prepared flavors made to simulate fruit or vegetable flavors derived from natural sources. Particularly preferred fruit flavors are the citrus flavors including orange, lemon, lime and grapefruit flavors. Besides citrus flavors, a variety of other fruit flavors can be used such as apple, grape, cherry, pineapple, mango and papaya flavors and the like. These fruit flavors can be derived from natural sources such as juices and flavor oils, or can be synthetically prepared. As used herein, the term "botanical flavor" refers to flavors derived from parts of a plant other than the fruit; i.e. derived from nuts, bark, roots and leaves, and beans such as coffee, cocoa, and vanilla. Also included within the term "botanical flavor" are synthetically prepared flavors made to simulate botanical flavors derived from natural sources. Examples of such flavors include cola, tea, coffee, chocolate, vanilla, almond, and the like. Botanical flavors can be derived from natural sources such as essential oils and extracts, or can be synthetically prepared.

The flavor component can comprise a blend of various flavors, e.g. lemon and lime flavors, cola flavors and citrus flavors to form cola flavors, etc. If desired, juices such as orange, lemon, lime, apple, grape, carrot, celery, and like juices can be used in the flavor component. The flavors in the flavor component are sometimes formed into emulsion droplets which are then dispersed in the beverage concentrate. Because these droplets usually have a specific gravity less than that of water and would therefore form a separate phase, weighting agents (which can also act as clouding agents) are typically used to keep the emulsion droplets dispersed in the beverage. Examples of such weighting agents are brominated vegetable oils (BVO) and rosin esters, in particular the ester gums. See L. F. Green, Developments in Soft Drinks Technology, Vol. 1, (Applied Science Publishers Ltd. 1978), pp. 87–93, for a further description of the use of weighting and clouding agents in liquid beverages. Besides weighting agents, emulsifiers and emulsion stabilizers can be used to stabilize the emulsion droplets. Examples of such emulsifiers and emulsion stabilizers include the gums, pectins, celluloses, polysorbates, sorbitan esters and propylene glycol alginates. See L. F. Green, supra at p. 92. The particular amount of the flavor component effective for imparting flavor characteristics to the beverages and beverage concentrates ("flavor enhancing") can depend upon the flavor(s) selected, the flavor impression desired, and the form of the flavor component. The flavor component can comprise at least 0.05% by weight of the beverage composition, and typically from 0.1% to 2% by weight for carbonated beverages. When juices are used as the flavor, the flavor component can comprise, on a single-strength basis, up to 25% fruit juice by weight of the beverage, preferably from 5% to 15% juice by weight for carbonated beverages.

Carbon dioxide can be introduced into the water which is mixed with the beverage syrup or into the drinkable beverage after dilution to achieve carbonation. The carbonated beverage can be placed into a container such as a bottle or can and then sealed. Any conventional carbonation methodology can be used to make the carbonated beverages of this invention. The amount of carbon dioxide introduced into the beverage will depend upon the particular flavor system used and the amount of carbonation desired. Usually, carbonated beverages of the present invention contain from 1.0 to 4.5 volumes of carbon dioxide. The preferred carbonated beverages contain from 2 to about 3.5 volumes of carbon dioxide.

The present invention is also particularly suited for the supplementation of beverages and beverage concentrates, including citrus juices. The beverages can contain from 3% to 100% juice or from about 0.05% to about 10% of an artificial or natural flavor, particularly orange juice. The concentrated orange juice, orange juice aroma and flavor volatiles, pulp and peel oils used in the method of the present invention can be obtained from standard orange juice. See Nagy et al, Citrus Science and Technology, Volume 2, (AVI Publishing Co. 1977), pp 177–252 for standard processing of oranges, grapefruit and tangerines. (See also Nelson et al, Fruit and Vegetable Juice Processing Technology (3rd Ed., AVI Publishing 1980), pp. 180–505 for standard processing of noncitrus juices such as apple, grape, pineapple, etc. to provide sources of juice and juice materials for noncitrus juice products).

Juices from different sources are frequently blended to adjust the sugar to acid ratio of the juice. Different varieties of oranges can be blended or different juices can be blended to get the desired flavor and sugar to acid ratio. A sugar to acid ratio of from about 8:1 to about 20:1 is considered acceptable for fruit juices. However, preferred sugar to acid ratios are typically from about 11:1 to about 15: 1, especially for citrus juices Sweeteners include the sugars normally present in juice products, for example glucose, sucrose, and fructose. Sugars also include high fructose corn syrup, invert syrup, sugar alcohols, including sorbitol, refiners syrup, and mixtures thereof. In addition to sugar, extended juice beverages of the present invention can contain other sweeteners. Other suitable sweeteners include saccharin, cyclamates, acetosulfam, L-aspartyl-L-phenylalanine lower alkyl ester sweeteners (e.g. aspartame). A particularly preferred sweetener for use in such extended juice products is aspartame. For single-strength juice beverages, the sugar content can range from about 2° to about 16° Brix (16° Brix means the juice contains about 16% soluble solid, and so on). Typically, the sugar content of such beverages depends upon the amount of juice contained herein. For full-strength beverages containing at least about 95% juice, the sugar content is typically from about 5° to about 14° Brix. For extended juice beverages which comprise from about 50% to about 90% juice, the sugar content is typically from about 5° to about 13° Brix (no other sweetener) or from about 2° to about 8° Brix (other sweetener containing). For juice concentrates according to the present invention, the sugar content can range from about 6° to about 75° Brix. Typically, the sugar content of these juice concentrates is from about 20° to about 50° Brix. For orange juice concentrates, the sugar content is preferably from about 35° to about 50° Brix.

The amount of the sweetener effective in the beverages of the invention depends upon the particular sweetener used and the sweetness intensity desired. For noncaloric sweeteners, this amount varies depending upon the sweetness intensity of the particular sweetener. For sugar, this amount can be from 1% to 14% (typically from 6% to 14%) by weight for carbonated beverages. Preferred beverages contain from 9% to 13% by weight sugar. In determining the amount of sugar for beverages of the present invention, any sugar or other sweetener present in he flavor component, such as in juice, is also included. Low-calorie sweetener combinations containing a noncaloric sweetener such as aspartame and a sugar such as high fructose corn syrup can also be used in beverages. For beverage syrups, the amount of sugar in a beverage syrup is from about 10% to about 60%, and preferably from about 40% to about 60%. In addition to sweeteners, beverages may also already be fortified with water soluble or fat soluble vitamins. The composition of this invention may be added to beverages that already contain or to which are later added vitamin compositions that are not of this invention.

The various beverage and beverage concentrates can be packaged in conventional packages for the particular beverage or beverage concentrates which are nutritionally supplemented by the optically clear composition of fat soluble vitamins. In some instances, the concentrates are frozen.

The powder compositions of this invention may also be added to cosmetics if it is desired to blend fat soluble vitamins such as vitamin E into a cosmetic. If the cosmetic is optically clear, preferred compositions of this invention may be used to avoid increasing the turbidity of the cosmetic. Cosmetics include any materials designed for application to the skin, hair, or nails, for example skin care products such as balms, lotions, or sticks, various ointments, make-up compositions for use on the face, eyes, or lips, shampoos and conditioners, nail polishes, and the like. The cosmetic may contain other active ingredients. Pharmaceutical compositions intended for topical application in the form of ointments, lotions, and the like are also contemplated. Cosmetic formulations will be well known to the skilled person. The powder composition of this invention is added at an appropriate time in the production process such as to be thoroughly blended into the cosmetic.

The powder composition of this invention which comprises droplets of a fat soluble vitamin which droplets average about 70 to about 200 nanometers in diameter (preferably about 80 to about 120 nm, and most preferably about 100 nm), and which are dispersed in a modified polysaccharide matrix can be made by combining water with the modified polysaccharide for a period of time sufficient for the modified polysaccharide to dissolve in the water. This can be done at any reasonable temperature to ensure a rapid dissolution of the modified polysaccharide in water and to fully utilize its functionality. To ensure complete dissolution of modified polysaccharide within a reasonable amount of time, heating to about 70° or 80° C. is preferable, after which the resulting solution may be conveniently cooled to about room temperature or a little higher (about 30°). Then fat-soluble vitamin is added to the solution and homogenized to form a crude emulsion with a emulsion droplet size of about 1500 nm or smaller, and emulsifying the crude emulsion at a temperature of about 5° C. to about 75° C. at a pressure of about 10,000 to about 60,000 psi to obtain a vitamin supplement emulsion containing vitamin droplets which average about 70 to about 200 nm in diameter. In order to attain the desired droplet size, the emulsion step may be repeated through one or more passes as necessary to obtain the desired droplet size, i.e. the crude emulsion is passed into the homogenization vessel, emulsified, passed out of the homogenization vessel, and passed through the homogenization vessel again until the desired droplet size is attained. Usually at least five to twenty passes will be required. These passes are usually all performed at the same pressure and the same system parameters, but different pressures may be used for different passes (other system parameters could also be varied for different passes). The period of time for one pass is not critical. The amount of time per pass will depend on system parameters including emulsion viscosity, batch size, flow rate and pressure. These parameters will depend on the precise processing format selected, and may be varied by the skilled person to obtain the desired results. Emulsification passes should continue until testing shows that the desired droplet size is achieved as determined by particle size analysis(for example by light scattering as described above). It is important that the homogenization step be performed at an ultra-high pressure as described above to effectively reduce the droplet size of the emulsion to a desirable size. The homogenization temperature as measured at the exit of the homogenizer is preferably below 70° C. The emulsion is then converted to a powder, by a known technology such as freeze-drying, fluid-bed drying, beadlet formation, but preferably by spray-drying, to obtain a powder composition which comprises droplets of a fat soluble vitamin which droplets average about 70 to about 200 nanometers in diameter (preferably about 80 to about 120, and most preferably 100 nm), and which are dispersed in a modified polysaccharide matrix. A powder composition produced by this process is part of this invention.

The final emulsion yields a powder which, upon redispersal in a liquid, yields an emulsion droplet size generally about 10–15 nm larger than the droplet size of the emulsion before spray drying. A powder so produced will contain vitamin droplets of 200 nm or less. Such a powder when added to a liquid, will provide droplets with average droplet size of about 70 to about 200 nm, preferably about 80 to about 120 nm, most preferably about 100 nm. Such droplet sizes are convenient for adding to beverages at fortification levels of up to about 5 to about 30 mg, preferably about 8 to about 20 and especially about 15 mg of vitamin per 8 ounce (240 g) serving of beverage. As discussed above, vitamin E may be added in pure form (i.e. 15 mg vitamin E per 8 oz). However, the more potent fat soluble vitamins will preferably be diluted, so that what is added would be 15 mg of vitamin in diluent rather than 15 mg of pure vitamin. When added, the resulting beverage should display no ringing. In addition, the added vitamin may be provided with superior bioavailability.

Figure 1:
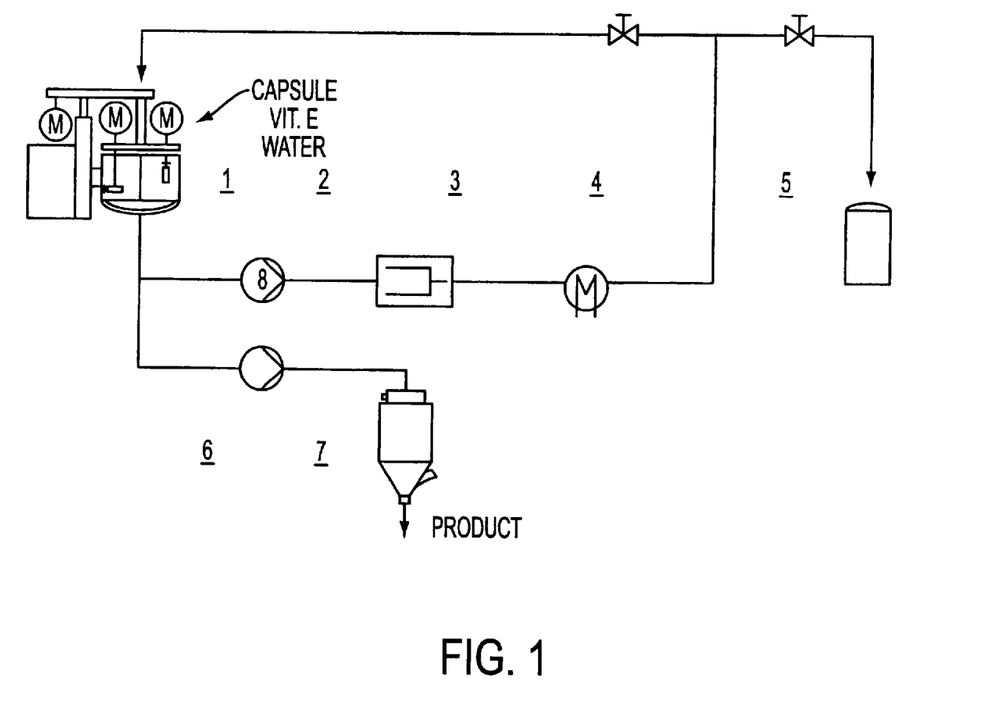
Figure 2:
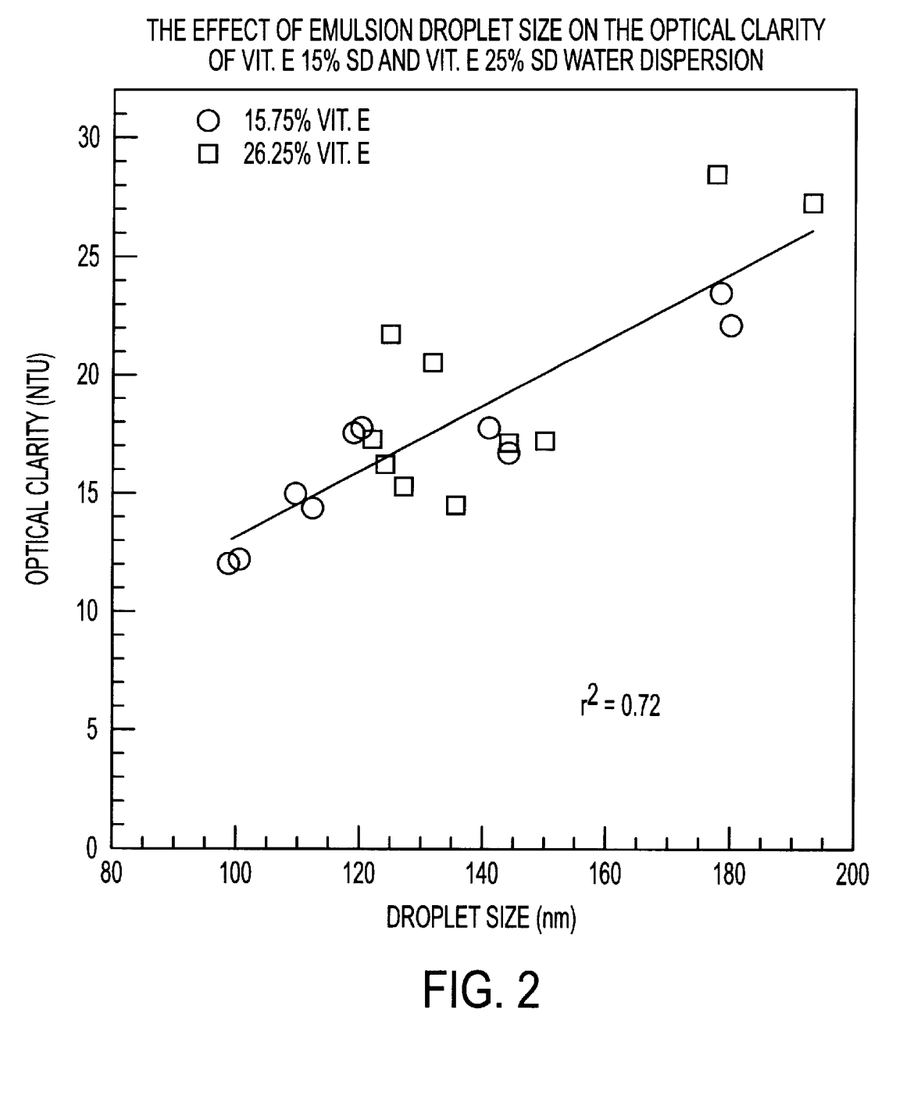
FIG. 2 . Graph of droplet size (nm) versus optical clarity (NTU) for 15.75% vitamin E (circle) and 26.25% vitamin E (square) in water dispersion.

With regard to an originally optically clear beverage, in order to maintain optical clarity a preferred composition of this invention may be added. The NTU of the resulting beverage should be no more than 30, and preferably around 10 to 15, especially at lower levels of fortification. In general, at the desired levels of fortification a droplet size of about 120 nm in diameter is acceptable with regard to optical clarity, and does not contribute substantial NTUs. In general a droplet of smaller size may be preferable for use at a higher level of fortification. Thus with regard to minimizing turbidity in an optically clear beverage, a powder with a higher average vitamin droplet size would be more useful at a lower level of fortification while a powder with a lower average vitamin droplet size would be preferable at a higher level of fortification. In this regard, FIG. 2 provides guidance on the relationship between droplet size and optical clarity. As can be seen by this best fit approximation, this relationship is roughly linear such that as droplet size increases, NTU increases for the same level of fortification. Thus optical clarity (NTU) is a function of the droplet size of the composition. However the potency of the powder does not have a significant effect on the relationship between turbidity and droplet size in the potency range of 15–25% percent.

To obtain the emulsion and powder of this invention, the parameters of the above process may be varied within the limits provided. The pertinent variables are pressure in the emulsification step, solids content, which is percent by weight in the crude emulsion of the vitamin(s) plus the modified polysaccharide(s), the lipid component of the solids content, which is the percent by weight of the solids content which is vitamin(s), including any edible diluent such as oil, and the number of passes through the emulsification step. Within the guidance of this invention these parameters may be varied to obtain a powder composition which contains vitamin droplets of 200 nm or less in diameter, and which has a potency (which is percent by weight of vitamin) of from about 0.5% to 75%, especially about 25% to about 40%, and which provides fortification levels of multiple RDAs of the vitamin, preferably about 1–3 RDA of vitamin, most preferably in the form of 5 to about 30 mg of vitamin (pure, or as processed in a diluent) per 8 ounces of liquid.

The potency of the powder of this invention is determined by the amount of fat soluble vitamin in the crude emulsion. For example, an emulsion which is about 5% to about 15% by weight vitamin (pure vitamin or vitamin in diluent) will in rough estimate provide a powder with a potency of about 10% to 30% by weight. However, a skilled person will be able to vary the emulsion content with the guidance provided by this invention to obtain a desired potency in the resulting powder.

In general, the lower the pressure, the more passes will be required to obtain an emulsion with a given droplet size. Also, the higher the lipid content, the more passes will be required to obtain the given droplet size. (as discussed above, the droplet size of the emulsion determines the droplet size in the resulting powder, and the droplet size in the liquid to which the powder is ultimately added is about 10–15 nm greater than the droplet size of the original emulsion). The potency of the powder is roughly twice the lipid content (for pure vitamin) of the emulsion. The emulsion is processed as described above, and in more detail below, to obtain the desired droplet size. If a high level of fortification is desired, then it is preferable to obtain a powder with droplet sizes at the low end of the range. Lower droplet sizes can be obtained by increasing the the processing pressure, or the number of passes. If it is possible to increase the processing pressure, then a given number of passes at the higher pressure will provide smaller droplets. However, if the pressure cannot be increased (if for example 15,000 psi is the upper limit for the equipment being used), then the same result can be obtained by increasing the number of passes.

With regard to obtaining a powder containing droplets of a size which provide an acceptable turbidity for the desired fortification level, the droplet size resulting from addition of the powder is the most important variable. It is possible to add less of a higher potency powder than of a lower potency powder to get the same level of fortification, but if the higher potency powder has a larger droplet size, then the fact that less of this powder is added will not negate the effect of the droplet size and higher turbidity will result.

To obtain powder compositions of this invention, the above parameters may be varied within the following limits: The pressure range is from about 10,000 psi to about 60,000 psi, preferably from about 20,000 to about 35,000 psi, and especially about 30,000 psi. The solids content is preferably no more than 60%, and the lipid content is 75% or less of the solids content. A preferred pressure is 20,000 to 35,000 psi, particularly 30,000 psi. A preferred crude emulsion has a solids content of from about 30% to about 50%, preferably about 45%, a preferred lipid content is from about 10% to about 50%. A preferred potency is from about 25% to about 40%. The number of passes that will be required to attain a droplet size in the emulsion of about 70 to about 200 nm may be adjusted depending on the parameters.

The various steps in the above method may be performed by known methods using conventional reagents and equipment. A skilled person given the guidance provided herein will be able to adjust the emulsion, solids and lipid content (for potency), pressure, and number of passes, within the limits of this invention, to readily obtain a powder composition of this invention.

In more detail, the powder is prepared by emulsifying a crude emulsion of fat soluble vitamin and modified polysaccharide (for example the emulsion of this invention). Once the emulsion has reached the desired emulsion droplet size, it is spray dried into a powder. The potency of the powder is the weight percent of vitamin which the powder contains.

The crude emulsion is prepared by combining the fat soluble vitamin with the modified polysaccharide in suitable amounts which will provide a powder product having a droplet size when dissolved in liquid of about 70 to 200 nm, preferably about 80 to about 120 nm and most preferably about 100 nm. An emulsion containing about 5–15% by weight of fat soluble vitamin, 30–40% by weight of modified polysaccharide, and 50–55% by weight water is an example. The emulsion may be prepared in a standard vessel of a convenient capacity where heating and cooling can take place. The water and modified polysaccharide are added to the vessel. The mixture may be heated to about 80° C., but this is not required. The mixture should be stirred until the modified polysaccharide has dissolved.

The solution is then left at or cooled to room temperature to about 30° C., and the fat soluble vitamin is slowly added. The mixture is homogenized to a crude emulsion in the vessel (for example by using a colloid mill or any other conventional mixing means) until the droplet size is less than 1500 nm. Droplet size may be measured by any conventional particle size analyzer. A preferred measuring means is laser light scattering technique. The Malvern ZetaSizer 3 or Autosizer lic (Malvern Instruments, Southborough, Mass.) is an example of a laser light scattering measuring device.

The crude emulsion is then further emulsified using standard equipment and vessels for this purpose. The device selected should provide a sufficiently high pressure. Microfluidizer devices are useful, such as models M-210C-E/H, M-110ET, M610-C, and M-140K may be obtained from Microfluidics International Corporation [Newton, Mass.]. It is also possible to use a water jet (such as those produced by Jet Edge Inc., Minneapolis, Minn.). The crude emulsion may be transferred from the holding vessel to the emulsifying device through a suitable sieve in order to prevent from clogging of the microfludizer. The temperature at which the homogenization (by which is meant further emulsification) takes place is best kept between room temperature (about 20–25° C.) or about 30° up to about 75° with a cooling system such as an ice water bath to control the temperature at high pressures. The pressure pump of the emulsifying device should be set at a suitable pressure (10,000 to 60,000 psi depending on the desired droplet size). Note that pressure in the device may fluctuate over a wide range depending on the number of pistons in the high pressure pump. A two-piston Microfluidizer varies from 7,250 to 14,500 psi (500 to 1000 bar). A three-piston pump is preferable.

Homogenization continues for a sufficient number of passes to obtain an emulsion of the desired droplet size. In general, the stabler the process pressure, the fewer number of passes should be required to achieve the same droplet size. The emulsion is then dried to obtain the powder of this invention. Drying may be accomplished by any standard method, for example spray-drying in a suitable spray dryer, such as a Yamato Mini-Spray Dryer.

The following examples served to demonstrate the present invention, but are not intended to limit it in any way.

EXAMPLES

Example 1

Starch sodium octenyl succinate (10 kg) was dissolved in 80° C. distilled water (14.5 kg). After the solution was cooled to about 30° C., vitamin E acetate (1.87 kg) was slowly added and homogenized with a colloid mill until the droplet size of the emulsion was below 1500 nm. The crude emulsion was homogenized with a Microfludics M-210-E/H at 700 bar. The emulsion was recycled through the homogenization process until the droplets of the emulsion reached about 104 nm. During the homogenization, the temperature of the emulsion was maintained at around 35° C. with a cooling system.

The emulsion was spray-dried using a Minor spray dryer (Model Hi-Tec) to yield a powder containing about 15% of vitamin E acetate. The powder was dissolved in water to give a turbidity about 18.9 NTU at a concentration of 15 mg vitamin E acetate per 240 g of water.

The amount of powder to be added to a beverage depends on the amount of fortification desired. It is important to determine the optimal particle size for the desired level of fortification.

The beverage or beverage concentrates supplemented with the compositions or tablets of fat soluble vitamins of the present invention can be made by conventional means well known to those of ordinary skill in the art. In general, the optically clear composition of fat soluble vitamins can be simply added and gently mixed into the beverage or beverage concentrates or syrups. The effervescent tablet is generally dropped into the beverage and allowed to dissolve (tablets do not generally yield an optically clear beverage due to other tabletting ingredients, but do give a beverage without ringing, provided that other ingredient do not themselves cause ringing). The beverage concentrates and syrups to which the powder composition of fat soluble vitamins has been added can be used to make final single strength beverage by blending the concentrate or syrup with an appropriate amount of water, usually about 1 part concentrate or syrup to about 3 to 4 parts of water. The water can be carbonated or non-carbonated.

TABLE 1

| | % Retention (based on initial assay) | | |
|---|---|---|---|
| Initial assay, % | 1 MO | 3 MO | 6 MO |
| 14.73 | 99.8 | 99.1 | 99.1 |

Apple juice and Lemon-Ice Gatorade were fortified with the spray-dried powder (16/96-10) at 8,15 and 30 mg vitamin. E acetate per serving (240 g) and preserved with 0.05% sodium benzoate. Control samples (0 mg) were also included. The samples were filled into 8-oz glass bottles to about 90% full and, after capped, pasteurized at 70° C. for 20 minutes The chemical stability of vitamin E acetate in water and beverages is shown in the following table. After 6 months at RT and 5° C., the average vitamin E retention were 92%, 102% and 101% in water, Gatorade and apple juice, respectively.

TABLE 2

Chemical Stability in beverages at Room temperature and 5° C.

| | | % Retention (based on initial assay) | | | | | | | |
|---|---|---|---|---|---|---|---|---|---|
| | | Room temperature | | | | 5 degrees C | | | |
| | IntialAssay mg/serving | 1 MO | 3 MO | 6 MO | 9 MO | 1 MO | 3 MO | 6 MO | 9 MO |
| Water | 14.9 | 102.7 | 91.9 | 87.9 | 96 | 106 | 99.3 | 81.9 | 103 |
| Gatorade | 15.7 | 101.3 | 99.4 | 101.9 | 97 | 104.5 | 91.1 | 113.4 | 97 |
| Apple Juice | 16.1 | 100.0 | 85.1 | 89.4 | 94 | 101.9 | 91.9 | 95.0 | 90 |

Examples of other beverages to which the powder compositions of fat soluble vitamins of this invention can be added in nutritionally supplemental amounts include:

(a) "sparkling" orange juice comprising 55% orange juice and 45% carbonated water;

(b) pear-grapefruit nectar comprising 25% pear juice, 20% grapefruit juice, the balance comprising 10% sucrose-water;

(c) kiwi-grapefruit drink comprising 20% kiwi fruit juice, 15% grapefruit juice, the balance comprising water;

(d) mixed fruit "cocktail" comprising 10% each of the juices of passion fruit, mango, guava, pineapple, papaya, banana, apricot, mandarin orange, pear and lime juices;

(e) yogurt/fruit beverage comprising 20% milk products, 1% pectin, 20% pineapple juice, 10% shredded pineapple fruit pulp, 16% corn syrup, the balance comprising water;

(f) cola beverage comprising 0.35% cola flavor emulsion, 11% sugar, 0.1% phosphoric acid, 0.1% citric and malic acids, caramel coloring, the balance comprising carbonated water;

(g) full-strength orange juice;

(h) full-strength apple juice;

(i) full-strength flavored cow's milk.

After 6 months at room temperature, there was no significant loss of vitamin E acetate in the spray dried powder as shown in the following table.

Up to 6 months, there is no ringing or precipitation resulted from vitamin E fortification. The spray dried powder can be used to fortify apple juice or Gatorade at about 8–12 mg vitamin E per serving to give a optical clarity as shown in Table 3.

TABLE 3

Optical clarity of vitamin E fortified apple juice and Gatorade at 5° C. and room temperature.

| | Turbidity[a], NTU | | | | | |
|---|---|---|---|---|---|---|
| | Apple Juice | | | Gatorade Lemon-Ice | | |
| | 0 mg | 15 mg | 30 mg | 0 mg | 15 mg | 30 mg |
| Before pasteurization | 4.4 | 16.3 | 27.2 | 4.5 | 16.0 | 29.7 |
| After pasteurization 5° C. | 3.6 | 13.5 | 24.6 | 4.1 | 15.5 | 27.6 |
| 1 wk | 3.9 | 14.4 | 24.1 | 3.8 | 16.2 | 29.5 |
| 2 wk | 3.9 | 14.7 | 24.6 | 3.8 | 16.8 | 30.5 |
| 3 wk | 3.5 | 14.4 | 24.9 | 3.7 | 17.0 | 31.2 |
| 1 MO | 3.5 | 14.9 | 25.0 | 3.7 | 17.5 | 32.7 |
| 2 MO | 3.5 | 15.2 | 25.7 | 3.7 | 18.4 | 34.3 |
| 3 MO | 3.5 | 15.4 | 26.1 | 3.5 | 19.4 | 36.4 |
| Room Temp. | | | | | | |
| 1 wk | 3.4 | 14.1 | 24.5 | 3.8 | 17.1 | 31.4 |
| 2 wk | 3.4 | 14.9 | 25.4 | 3.8 | 18.7 | 33.3 |
| 3 wk | 3.5 | 14.9 | 26.1 | 3.5 | 19.5 | 35.2 |
| 1 MO | 3.4 | 15.6 | 26.7 | 3.5 | 20.4 | 37.1 |

TABLE 3-continued

Optical clarity of vitamin E fortified apple juice and Gatorade at 5° C. and room temperature.

| | Turbidity[a], NTU | | | | | |
|---|---|---|---|---|---|---|
| | Apple Juice | | | Gatorade Lemon-Ice | | |
| | 0 mg | 15 mg | 30 mg | 0 mg | 15 mg | 30 mg |
| 2 MO | 4.1 | 16.2 | 27.4 | 3.3 | 22.7 | 43.1 |
| 3 MO | 7.4[b] | 17.7 | 31.0 | 3.3 | 25.6 | 51.4 |

[a]Apple juice (prepared from Seneca Red Frozen Juice concentrate) and Gatorade Lemon Ice were fortified at 8, 15, and 30 mg per serving (240 g).
[b]Microbial spoilage was noticed.

Example 2

Starch sodium octenyl succinate (2511 g) was dissolved in a 80° C. distilled water (2960 g). After the solution was cooled to about 30° C., vitamin E acetate (454.6 g) was slowly added while being homogenized with a Gifford-Wood 1L homogenizer at high speed for 3 minutes. The crude emulsion was homogenized at about 9000 psi with Microfluidics M-110 at a flow rate of about 560 ml per minute. The emulsion was recycled through the homogenization process until the droplets of the emulsion reached about 116 nm after approximately 19 passes. During the homogenization, the temperature of the emulsion was kept at around 35° C. with a cooling system.

The emulsion was dispersed in water to give a turbidity of 12.3 NTU at a concentration of 15 mg vitamin E acetate per 240 g of water.

Example 3

Starch sodium octenyl succinate (2340.4 g) was dissolved in a 80° C. distilled water (2392.3 g). After the solution was cooled to about 30° C., vitamin E acetate (1576.4 g) was slowly added while being homogenized with a lab homogenizer until the droplet size was below 1500 nm. The emulsion was filtered through a 50-mesh sieve to remove any undissolved large particles. The crude emulsion was homogenized at a pressure of about 15,000 psi with a high pressure homogenizer (Microfludics M-110). The emulsion was recycled through the homogenization process until the droplets of the emulsion reached about 125 nm. During the homogenization, the temperature of the emulsion was kept at around 25 to 35° C. with a cooling system.

The emulsion was spray dried (Yamato Mini Spray Dryer; Model ADL-31) to give the vitamin E powder. The emulsion droplet size of the powder in water was about 136 nm.

The vitamin E powder, which contained 42.5% vitamin E, was used to fortify Gatorade and apple juice at 15 mg of vitamin E acetate per serving (240 g). To do the fortification, appropriate amount of the powder was dissolved in the beverages and the fortified beverages were pasteurized at 90° C. The optical clarity of the beverages was determined before and after pasteurization and the results are shown in the following table.

TABLE 4

| | Turbidity, NTU* | |
|---|---|---|
| | Gatorade Lemon Ice | Seneca Apple Juice |
| Before Pasteurization | 56.5 | 48.6 |
| After Pasteurization | 55.6 | 47.8 |

*the concentration was 15 mg vitamin E acetate per 240 g/8 oz. beverage

Fortification to about 6–8 mg per 8 oz. serving would provide a turbidity level below 30 NTU with this composition. Alternatively, the emulsion could be processed through further passes in order to obtain an emulsion droplet size of about 110 nm or below, which would provide a powder which could be added to a beverage at 15 mg/8 oz. at a turbidity below 30 NTU.

Example 4

Starch sodium octenyl succinate (29.64%) was dissolved in a 80° C. distilled water (53.04%). After the solution was cooled to about 30° C., dl-α-tocopherol (17.32%) was slowly added and homogenized with colloid mill until the droplet size of the emulsion was below 1500 nm. The crude emulsion was homogenized with a Microfludics M-210-E/H at 1250 bar. The emulsion was recycled through the homogenization process until the droplets of the emulsion reached about 105 nm. During the homogenization, the temperature of the emulsion was kept at around 35° C. with a cooling system.

The emulsion was spray dried using a Minor spray dryer (Model Hi-Tec) to yield a dl-α-tocopherol powder with a droplet size in water of about 161 nm. The turbidity was 41 NTU at 15 mg vitamin E per 240 g of water (The fortification level was based on the assumption of no loss of vitamin E during the processing).

Example 5

Effervescent Tablets

Tablets were produced from the powder of Example 1 at 26.24% and Example 3 at 42.5% as shown below, and compared with tablets produced from a current 50% vitamin E powder product (see Table 5). The 50% vitamin E powder used for comparison may be obtained from Roche Vitamins and Fine Chemicals, Nutley, N.J.

TABLE 5

| Material | Lot No. |
|---|---|
| Dry Vitamin E 26.25% SD | 16196-8 (produced as described in Ex. 1) |
| Dry Vitamin E 42.5% SD | 27903-076 (produced as described in Ex. 2) |
| Dry Vitamin E 50% Type CWS/F | 51 23 49 |

An antioxidant formulation was chosen for the test. In this formula after the dissolution of the tablets very small oil droplets of Vitamin E (Dry Vitamin E 50% powder, Type CWS/F) may be seen in the surface of the water if the surface is observed very carefully against reflected light.

Tabletting Characteristics

Formula

Antioxidant: (6 mg/200 mg/50 mg)

(Beta Tab 10%E/Ascorbic Acid, Fine Granular/ Dry Vitamin E.50%, Type CWS/F)

TABLE 6

Effervescent Tablet

| Composition | Label Claim mg | Ovrg. % | E 26.25% Quantities mg/Tabl. | E 42.1% Quantities mg/Tabl. | E 50.0% Quantities mg/Tabl. |
|---|---|---|---|---|---|
| 1 Beta-Carotene | 6.00 | 20 | | | |
| as Beta Tab 10% E | | | 72.00 | 72.00 | 72.00 |
| 2 Vitamin C | 200.00 | 10 | | | |
| as Ascorbic Acid, Fine Granular | | | 220.00 | 220.00 | 220.00 |
| 3 Vitamin E | 50.00 | 10 | | | |
| as Dry Vitamin E 26.25% SD Lot 16/96-8 | | | 209.52 | | |
| as Dry Vitamin E 42.1% SD Lot 27903-076 | | | | 130.64 | <110 |
| 4 Citric Acid Anhydrous, Medium Granular | | | 1300.00 | 1300.00 | 1300.00 |
| 5 Sodium bicarbonate | | | 800.00 | 800.00 | 800.00 |
| 6 Sodium carbonate | | | 80.00 | 80.00 | 80.00 |
| 7 Mannitol MG[1] | | | 1138.48 | 1217.36 | 1238.00 |
| 8 Aspartame | | | 20.00 | 20.00 | 20.00 |
| 9 Sodium cyclamate | | | 30.00 | 30.00 | 30.00 |
| 10 Polyethylene Glycol 6000 Fine Powder[2] | | | 100.00 | 100.00 | 100.00 |
| 11 Orange flavor Permaseal 74016-71[3] | | | 20.00 | 20.00 | 20.00 |
| 12 Tangerine flavor Permaseal 74740-31[3] | | | 10.00 | 10.00 | 10.00 |
| Total Tablet Weight | | | 4000.00 | 4000.00 | 4000.00 |

Suppliers
[1]Mannitol medium granular Roquette Frères, 4 rue Patou, F-59022 Lille Cedex, France
[2]Hoechst AG, Postfach 800320 Frankturt/Main 80, F.R. Germany
[3]Givaudan Dübendorf AG, CH-8600 Dübendorf, Switzerland Procedure I Pass 3–12 through 1.00 mm sieve and mix with 1 and 2 for 15 minutes II Compress into effervescent tablets Tabletting Characteristics

| | E 26.25% | E 42.1% | E 50% |
|---|---|---|---|
| Tabletting machine | Comprex II | Comprex II | Comprex II |
| Punch | 25 mm FFBE coated | 25 mm FFBE coated | 25 mm FFBE coated |
| Compression force | 50 KN | 50 KN | 50KN |
| Hardness | 65N | 63N | 77N |
| Friability | 1.0% | 1% | 1.0% |
| Disintegration Time | 2 min 15 sec | 2 min. 5 sec. | min. 45 sec. |

Results

Both samples tested gave tablets from the 26.25% and 42.5% vitamin E powders of this invention with acceptable hardness and disintegration characteristics. Their compression profiles are very close to that of E 50% CWS/F. The disintegration time was no longer than 135 sec. Sample 27903-076 containing 42.5% vitamin E showed better hardness and slightly shorter disintegration time than the other.

On visual inspection of the surface of the water after the disintegration of the tablets made from the 26.25% and 42.5% vitamin E powders of this invention did not show any oily droplets. In contrast, oily droplets were visible on the surface of water with the vitamin E 50% CWS/F product not made from a composition of this invention.

Example 6

A vitamin conditioning shampoo may be produced using standard ingredients and methods as follows using a powder composition of this invention. Vitamin E acetate is used as an example: Disperse the vitamin E acetate powder into water. Add the vitamin E acetate powder to a mixture of Monamid and phytantriol. Add the panthenol and etyl panthenol. Add Part 2 to Part 1 and mix till clear. Add the Kathon CG and perfume. Adjust the pH with citric acid 50% solution to pH 6.0 to 6.8. Adjust the viscosity with sodium chloride.

| Ingredients | CTFA designation | % by weight |
|---|---|---|
| Part 1 | | |
| Deionized water | water | 57.05 |
| Monamid 716 | lauramide DEA | 5.00 |
| liquid DL-panthenol-50% | panthenol and water | 2.00 |
| 25% vitamin E acetate power | tocopheryl acetate | 0.80 |
| phytantriol | phytantriol | 0.10% |
| Part 2 | | |
| Standapol ES-2 | sodium laureth sulfate | 30.00 |
| Mirataine CBS | cocamidopropyl hydroxysultaine | 3.00 |
| Part 3 | | |
| sodium chloride | sodium chloride | 1.00 |
| citric acid 50% solution | citric acid | 0.30 |
| perfume | fragrance | 0.20 |
| Kathon CG | methylchloroisothiazolinone (and) methylisothiazolinone | 0.05 |
| | | 100 |

What is claimed is:

1. A powder composition which comprises droplets of a fat soluble vitamin which droplets average about 70 to about 200 nanometers in diameter, and which are dispersed in a modified polysaccharide matrix.

2. A composition of claim 1 wherein the droplets average about 80 to about 120 nanometers in diameter.

3. A composition of claim 2 wherein the droplets average about 100 nm in diameter.

4. A powder composition of claim 1 wherein the amount of fat soluble vitamin is from about 15 to about 40 percent by weight.

5. A powder composition of claim 4 wherein the amount of fat soluble vitamin is about 25% by weight of the powder.

6. A powder composition of claim 1 wherein the fat-soluble vitamin is selected from the group consisting of vitamin E or its esters, vitamin A or its esters, vitamin K, and vitamin D3.

7. A powder composition of claim 1 wherein the modified polysaccharide is a modified starch.

8. A powder composition of claim 7 wherein the modified starch is a compound of $$St-O-\underset{\underset{O}{\|}}{C}-R-R' \quad \text{with} \quad Na^+O-\underset{\|}{C}=O \text{ attached}$$

Formula 1 wherein St is a starch, R is an alkylene radical and R' is a hydrophobic group.

9. A powder composition of claim 8 wherein the fat soluble vitamin is vitamin E and the compound of Formula 1 is starch sodium octenyl succinate.

10. A powder composition of claim 8 wherein the fat soluble vitamin is vitamin E acetate and the modified polysaccharide is starch sodium octenyl succinate.

11. An emulsion composition which comprises a fat soluble vitamin; a modified polysaccharide; and water, wherein the droplets of the emulsion are no more than about 70 to about 200 nanometers in diameter.

12. An emulsion composition of claim 10 which comprises about 5% to about 15% by weight of a fat soluble vitamin; about 30% to about 40% by weight of a modified polysaccharide; and about 50% to about 55% by weight water.

13. An emulsion composition of claim 11 which comprises about 7.5% by weight to about 20% by weight of a fat-soluble vitamin.

14. An emulsion composition of claim 11 which additionally comprises a preservative.

15. A beverage comprising a mixture of
  (a) at least about 0 to 100% by weight of flavor and 0 to 100% by weight of juice;
  (b) a nutritionally supplemental amount of a fat-soluble vitamin, and a modified polysaccharide, and
  (c) water if necessary to bring the beverage weight to 100%; which beverage has an optical clarity of no more than 20 NTUs.

16. A beverage comprising a mixture of
  (a) at least about 0 to 100% by weight of flavor and 0 to 100% by weight of juice;
  (b) a modified polysaccharide, and a nutritionally supplemental amount of a fat-soluble vitamin in the form of droplets which average from about 70 to about 200 nanometers in diameter; and
  (c) water if necessary to bring the beverage weight to 100%.

17. A beverage of claim 16 which contains 0% flavor and 0% juice.

18. A beverage of of claim 16 wherein the fat-soluble vitamin is selected from the group consisting of vitamin E or its esters, vitamin A or its esters, vitamin K, and vitamin D3.

19. A beverage of claim 16 wherein the modified polysaccharide is a modified starch.

20. A beverage of claim 16 wherein the modified starch is a compound of

Formula 1

$$St-O-\underset{\underset{O}{\|}}{C}-R-R' \quad \text{with} \quad Na^+O-\underset{\|}{C}=O \text{ attached}$$

wherein St is a starch, R is an alkylene radical and R' is a hydrophobic group.

21. A beverage of claim 20 wherein the fat soluble vitamin is vitamin E and the compound of Formula 1 is starch sodium octenyl succinate.

22. A beverage of claim 20 wherein the fat soluble vitamin is vitamin E acetate and the modified polysaccharide is starch sodium octenyl succinate.

23. A beverage of claim 22 wherein the nutritionally supplemental amount of vitamin is from about 8 to about 20 milligrams of vitamin per 8 ounces of beverage.

24. A beverage of claim 16 wherein the droplets are from about 80 to about 120 nm in diameter.

25. A beverage of claim 16 which additionally contains a sweetener.

26. An effervescent tablet comprising a powder composition which comprises droplets of a fat soluble vitamin which droplets average about 70 to about 200 nanometers in diameter, and which are dispersed in a modified polysaccharide matrix.

27. A method for producing a powder composition which comprises droplets of a fat soluble vitamin which droplets average about 70 to about 200 nanometers in diameter, and which are dispersed in a modified polysaccharide matrix, which comprises:
  a. combining water with the modified polysaccharide for a period of time sufficient for the modified polysaccharide to dissolve in the water;
  b. adding fat-soluble vitamin to the solution of step a to form a crude emulsion;
  c. mixing the crude emulsion of step b until the size of the droplets within the emulsion is determined to be 1500 nm or less;
  d. emulsifying the crude emulsion of step c at a pressure of about 10,000 to about 60,000 psi to obtain a vitamin supplement emulsion consisting of droplets with average sizes of about 70 to about 200 nm; and e. drying the emulsion of step d to obtain a powder composition which comprises droplets of a fat soluble vitamin which droplets average about 70 to about 200 nanometers in diameter, and which are dispersed in a modified polysaccharide matrix.

28. A process of claim 27 wherein the pressure is 25,000 psi.

29. A process of claim 27 wherein the crude emulsion has a solids content of 45%.

30. A process of claim 27 wherein the temperature is maintained at about 5° C. to about 75° C.

31. A powder composition produced by the method of claim 27.

32. A powder composition wherein the droplets of fat soluble vitamin average about 80 to about 120 nm in diameter.

* * * * *